United States Patent
Lorenzoni et al.

[11] Patent Number: 5,262,016
[45] Date of Patent: Nov. 16, 1993

[54] PROCESS FOR PURIFYING PHENOL

[75] Inventors: Loreno Lorenzoni, Porto Torres; Salvatore Simula, Ittiri; Giuseppe Messina, Alghero; Vittorio Bruzzi, Milan, all of Italy

[73] Assignee: Enimont Anic S.r.l., Palermo, Italy

[21] Appl. No.: 705,395

[22] Filed: May 24, 1991

[30] Foreign Application Priority Data
Jun. 1, 1990 [IT] Italy .................. 20514 A/90

[51] Int. Cl.$^5$ .............................. B01D 3/40
[52] U.S. Cl. .................... 203/62; 203/74; 203/77; 203/80; 568/913
[58] Field of Search .......... 203/62, 74, 77, 80; 568/913

[56] References Cited

U.S. PATENT DOCUMENTS

| | | | |
|---|---|---|---|
| 2,537,115 | 1/1951 | Scheibel | 203/62 |
| 3,696,006 | 10/1972 | Huermann | 203/62 |
| 4,455,198 | 6/1984 | Zudkevitch et al. | 203/62 |
| 4,501,645 | 2/1985 | Berg et al. | 203/62 |
| 4,836,896 | 6/1989 | Berg | 203/62 |

FOREIGN PATENT DOCUMENTS

| | | |
|---|---|---|
| 0004168 | 9/1979 | European Pat. Off. |
| 0028522 | 10/1980 | European Pat. Off. |
| 0920905 | 3/1963 | United Kingdom |
| 1021759 | 3/1966 | United Kingdom |
| 1381398 | 1/1975 | United Kingdom |

Primary Examiner—Virginia Manoharan
Attorney, Agent, or Firm—Shea & Gould

[57] ABSTRACT

A stream of raw phenol, coming from the acidic cracking of cumene hydroperoxide, is purified by a process of extractive distillation carried out in the presence of acetophenone.

3 Claims, 1 Drawing Sheet

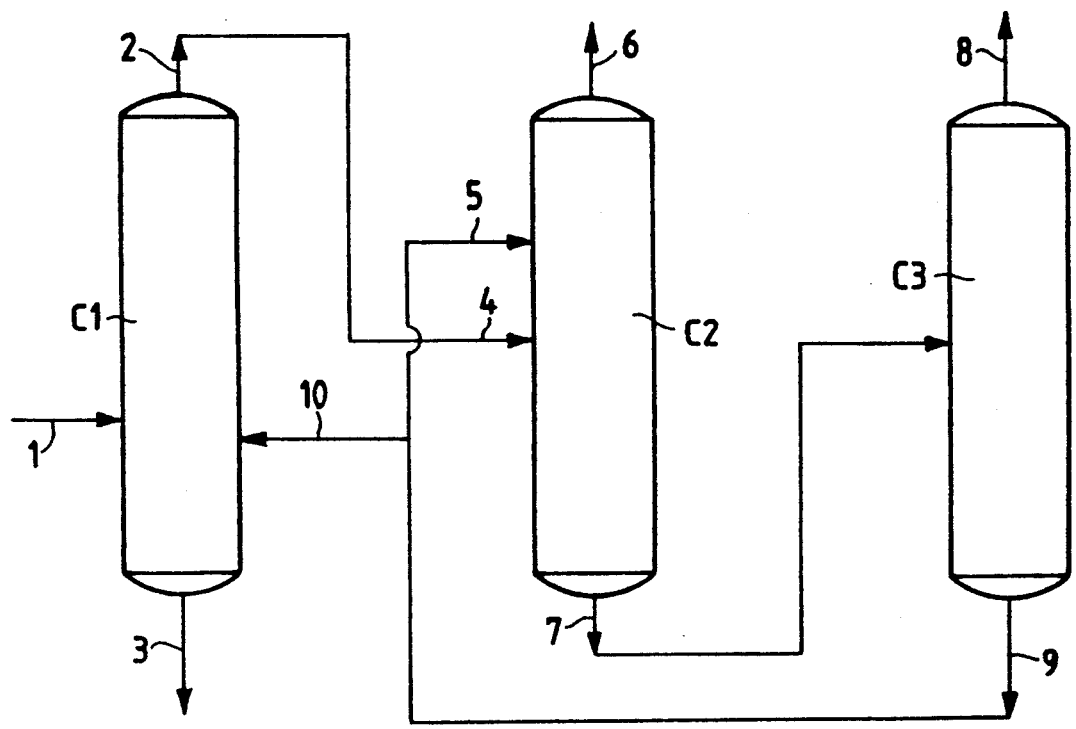

PROCESS FOR PURIFYING PHENOL

The present invention relates to an improved process for purifying phenol obtained by the acidic cracking of cumene hydroperoxide, a process according to which a phenol containing stream, after the preliminary separation of heavy components, is submitted to an extractive distillation in the presence of acetophenone.

The processes for producing phenol by means of the oxidation of cumene to cumene hydroperoxide and subsequent cracking of thus obtained hydroperoxide, in the presence of acidic catalysts, is known; the product from the acidic cracking contains phenol and acetone, as main products, besides minor amounts of different byproducts.

The fractional distillation of the cracked product makes it possible to produce phenol with a satisfactory purity for several uses. However, in the production of compounds such as bis-phenol, polycarbonate or nylon, a phenol with a very high purity is always required, which cannot be easily obtained by the treatments known from the prior art.

In general, the purity of phenol is checked by a color-development test after nitration, chlorination or sulfonation, in that these tests are generally very sensitive to the presence of chromogenic impurities. A very pure phenol is a phenol which in theses tests does not practically generate a color. Therefore, the normal purification of phenol is carried out by means of successive steps of fractional distillation, whilst the removal of the color-generating impurities is usually obtained by means of special treatments. For that purpose, treatments with acidic condensing agents have been proposed (German Patent Application 2,211,616), acidic silica-aluminates used at high temperatures, generally higher than 200° C. (U.S. Pat. No. 3,454,653), alkali and ferric chloride (British Patent 920,905), polyamines (U.S. Pat. No. 3,965,187) and hydrogen peroxide in an alkaline medium (U.S. Pat. No. 2,971,893).

All these treatments show one or more disadvantages, such as high cost, problems of regeneration of the agent used in the purification treatment, and problems deriving from the introduction of foreign chemical substances in the substance which one wishes to purify. Furthermore, these treatments make it difficult to obtain a complete or substantially complete removal of phenol impurities.

Also phenol purification processes have been proposed, which are based on distillation treatments, such as, e.g., disclosed in British Patent 1,021,759, and in European Patent Application publication No. 4,168.

Unfortunately, such distillation processes are difficult to carry out, in that they require a strict control of the operating conditions: in any case, although they make it possible to remove particle carbonylic compounds such as hydroxy-acetone and mesityl oxide up to a satisfactory extent, such processes are not suitable for separating all color-generating substances up to a complete, or substantially complete, extent.

The present Applicant has found now, what is the subject-matter of the present invention, that phenol free, or substantially free, from all of the above listed impurities, can be produced by means of a simple and advantageous process which essentially consists in sending a stream of raw phenol, previously deprived of its heavy components, to an extractive distillation in the presence of acetophenone which is fed to the head of the distillation tower and which, as known, is present as a byproduct normally removed together with the heavy components in the phenol production process carried out by starting from cumene hydroperoxide.

Although this is a procedure sometimes followed in the art, the recovery of acetophenone from these heavy components is not particularly favorable from an economic viewpoint, in that it is difficult to obtain acetophenone with the desired purity.

The present process, besides making it possible to produce phenol at a very high purity level, therefore useful for the above mentioned uses, shows the considerable advantages, as compared to the method known from the prior art, that it does not require the addition of foreign bodies, and reduces to a minimum the impurities of cresol type, which are difficult to remove according to the treatments used to date.

Furthermore, by using acetophenone as the extracting agent, said process makes it possible to use a portion of said acetophenone present as byproduct with the costs connected with the use of extracting solvents foreign to the process being thus avoided.

BRIEF DESCRIPTION OF THE DRAWING

The FIGURE shows a flow diagram of an embodiment of the process according to the present invention.

Referring to the scheme of the FIGURE, a stream from phenol facility, obtained according to the well-known route of acidic cracking of cumene hydroperoxide, from which, through several distillation steps, acetone, cumene, alpha-methyl-styrene have been separated, and therefore having a composition broadly comprised within the following limits:

| | |
|---|---|
| Phenol | 79–91,85% |
| Acetone | 0,1% |
| Cumene | 0,1–0,5% |
| Alpha-methyl-styrene | 0,1–3,0% |
| Mesityl oxide | 0,01–0,1% |
| Acetophenone | 1,6–3% |
| Dimethyl-phenyl-carbinol | 0,1–1,5% |
| Hydroxyacetone | 0,04–0,3% |
| Water | 0,1–0,5% |
| Pitches | 6–12% | is fed (through Line 1) to a distillation tower ($C_1$), operated in such a way as to separate an overhead stream (2) constituted by:

| | |
|---|---|
| Phenol | 90,6–99,24% |
| Acetone | 0,2–0,5% |
| Cumene | 0,1–0,6% |
| Alpha-methyl-styrene | 0,1–3,0% |
| Mesityl oxide | 0,01–0,1% |
| Acetophenone | 0,1–3,0% |
| Dimethyl-phenyl-carbinol | 0,1–1,0% |
| Hydroxyacetone | 0,04–0,3% |
| Water | 0,1–0,8% |
| other impurities among which o-, m-, p-cresol, paraffinic and ketonic impurities, benzofurans, and so forth) | 0,01–0,1% |

On the contrary, from the bottom (3) on the above said tower the pitches are separated, which are mainly constituted by cumyl-phenols, dimers of alpha-methyl-styrene and heavier pitches, plus the residual amount of acetophenone and dimethyl-phenyl-carbinol, not separated in the overhead stream.

The overhead product, having the above said composition, is fed to an intermediate point (4) of a distillation tower ($C_2$) operating under extractive conditions, to the head of which (5) the extracting agent is fed, which is essentially constituted by acetophenone and phenols in mutual ratios comprised within the range of the azeotropic mixtures of phenol and acetophenone under the operation conditions of the subsequent tower ($C_3$) plus, possibly, small excess amounts of phenol and other impurities.

The amount of this stream should be such as to keep, in tower $C_2$, the ratio of total acetophenone to total phenol at a value constantly comprised within the range of from 1 to 4. The above said tower ($C_2$) can be both operated at atmospheric pressure and at lower-than-atmospheric or higher-than-atmospheric pressures; pressure values close to atmospheric pressure are preferred.

By operating under these conditions, from the head of the above said tower (6) an overhead stream is separated in an amount comprised within the range of from 0.5 to 10% of the feedstock stream, which is essentially constituted by phenol plus all the light impurities and some heavy impurities and, in particular, acetone, cumene, alpha-methyl-styrene, mesityl oxide, hydroxyacetone, water, and portions of paraffinic, ketonic and benzofuran impurities.

The bottom stream from the above said tower (7), constituted by phenol purified from impurities and acetophenone, with residual amounts of dimethyl-phenyl-carbinol plus other heavy impurities, is fed to the subsequent tower ($C_3$), from whose head (8) pure phenol is separated as the overhead stream, and whose bottom stream (9) is constituted by the azeotropic phenol-/acetophenone mixture plug, possibly, residual amounts of phenol not separated in the overhead stream, and other heavy impurities, such as ortho-, meta-, para-cresol which, as phenol, generate, together with acetophenone, maximum-boiling-temperature azeotropic mixtures.

The operating pressure in tower $C_3$ can be the atmospheric pressure, a lower-than-atmospheric pressure, or a higher-than-atmospheric pressures.

The bottom product is totally or partially recycled to the tower $C_2$, in which it performs the task of extracting agent (5).

In order to keep the ratio of acetophenone to phenol comprised within the preset limits, respectively comprised within the range of from 1 to 4, and in order to prevent the heavy impurities from accumulating, a portion of this stream is recycled to tower $C_1$ (10).

EXAMPLE NO. 1

2000 grams/hour of a stream from phenol facility, obtained by means of the acidic cracking of cumene hydroperoxide, from which acetone, cumene and alpha-methyl-styrene have been previously distilled off, and having the composition as reported in the following table ("$C_1$ Feed" column), is fed to a distillation tower operating under vacuum. Inside this tower, an overhead stream (1840 g/h) of raw phenol is separated, which has the composition shown in the following table in "$C_1$ Overhead" column, and therefore is constituted by phenol plus all of the light impurities and a portion of heavy impurities, among which acetophenone, and, as the bottom stream, 160 g/h of heavy products, is separated.

The $C_1$ overhead product is fed to a subsequent tower operating under extractive conditions, together with the extracting agent coming from the bottom of $C_3$ tower, with a flow rate of 4700 g/h, and essentially constituted by acetophenone (70%), with the balance to 100% being phenol and heavy impurities.

In tower $C_2$, 162 g/h is separated as an overhead stream having the composition shown in the following table as "$C_2$ Overhead", and essentially constituted by phenol and practically all of the light impurities.

The bottom product, consisting of phenol and acetophenone, and heavy impurities, is rectified in a subsequent tower from which 1665 g/h of phenol containing extremely small amounts of impurities (total impurities < 100 ppm) is separated as the overhead stream. Said phenol has such a purity level as to pass the most strict tests of sulfonation, nitration and clorination.

|  | $C_1$ Feed | $C_1$ Overhead | $C_1$ Bottom | $C_2$ Overhead |
|---|---|---|---|---|
| Acetone | 0.1 | 0.3 | / | 3.4 |
| Mesityl oxide | 0,017 | 0.018 | / | 0.20 |
| Cumene | 0.38 | 0.4 | / | 4.53 |
| Butylbenzenes | 0.03 | 0.03 | / | 0.34 |
| Unidentified impurities | 0.1 | 0.1 | / | 1.11 |
| alpha-Methyl-styrene | 1.5 | 1.8 | / | 22.35 |
| Hydroxyacetone | 0.12 | 0.13 | / | 1.47 |
| Benzofurans | 0.004 | 0.004 | / | 0.04 |
| Acetophenone | 1.6 | 0.5 | 14.2 | / |
| Dimethylphenyl-carbinol | 1.17 | 0.2 | 6.0 | / |
| Phenol | 89.639 | 96.08 | 10 | 61.57 |
| o-, m-, p-Cresol | 0.05 | 0.028 | 0.3 | / |
| o-Cumyl-phenol | 0.4 | / | 5.5 | / |
| Dimethyl-alpha-methyl-styrene | 1.48 | / | 18.5 | / |
| p-Cumyl-phenol | 1.6 | / | 20.4 | / |
| Other impurities | 1.5 | / | 18.75 | / |
| Water | 0.31 | 0.41 | / | 4.94 |

We claim:

1. Process for purifying phenol coming from the acidic cracking of cumene hydroperoxide, which purification process consists essentially of submitting a stream of phenol comprised of phenol and light impurities from an overhead discharge of a distillation tower to an extractive distillation in the presence of acetophenone in a second distillation tower to form a second stream of phenol comprised of phenol and heavy impurities as a bottom stream from the second distillation tower, and thereafter subjecting said second stream to a rectification to yield phenol having less than about 100 ppm of impurities as an overhead stream.

2. Process for purifying phenol according to claim 1 wherein the extractive distillation is carried out at a ratio of total acetophenone to total phenol comprised within the range of from 1 to 4.

3. Process for purifying phenol according to claim 1, wherein the stream of phenol contains phenol in amounts comprised within the range of from 90 to 99.5%.

* * * * *